United States Patent
Harrell

(10) Patent No.: US 11,633,432 B2
(45) Date of Patent: *Apr. 25, 2023

(54) AMNIOTIC FLUID TOPICAL FORMULATION

(71) Applicant: MAM Holdings of West Florida, L.L.C., Tarpon Springs, FL (US)

(72) Inventor: Carl Randall Harrell, Tarpon Springs, FL (US)

(73) Assignee: MAM HOLDINGS OF WEST FLORIDA, L.L.C., Palm Harbor, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/023,041

(22) Filed: Jun. 29, 2018

(65) Prior Publication Data

US 2018/0311284 A1 Nov. 1, 2018

Related U.S. Application Data

(63) Continuation of application No. 15/289,632, filed on Oct. 10, 2016, now abandoned.

(60) Provisional application No. 62/239,677, filed on Oct. 9, 2015.

(51) Int. Cl.
| | | |
|---|---|---|
| A61K 35/50 | (2015.01) | |
| A61K 9/00 | (2006.01) | |
| A61K 9/08 | (2006.01) | |
| A61K 9/19 | (2006.01) | |
| A61K 47/10 | (2017.01) | |

(52) U.S. Cl.
CPC ............ A61K 35/50 (2013.01); A61K 9/0048 (2013.01); A61K 9/0051 (2013.01); A61K 9/08 (2013.01); A61K 9/19 (2013.01); A61K 47/10 (2013.01)

(58) Field of Classification Search
None
See application file for complete search history.

(56) References Cited

U.S. PATENT DOCUMENTS

| | | |
|---|---|---|
| 1,699,479 A | 1/1929 | Scott |
| 3,752,158 A | 8/1973 | Kariher |
| 4,308,875 A | 1/1982 | Young |
| 4,977,897 A | 12/1990 | Hurwitz |
| 5,000,192 A | 3/1991 | Sealfon |
| 5,219,576 A | 6/1993 | Chu |
| 5,436,135 A | 7/1995 | Tayot |
| 5,698,228 A | 12/1997 | Takai |
| 5,997,896 A | 12/1999 | Carr, Jr. |
| 7,871,646 B2 | 1/2011 | Ghinelli |
| 7,928,280 B2 | 4/2011 | Hariri |
| 8,372,439 B2 | 2/2013 | Daniel |
| 9,132,156 B1 | 9/2015 | Werber .................. A61K 35/50 |
| 9,579,350 B1 | 2/2017 | Harrell .................. A61K 35/50 |
| 2004/0057938 A1 | 3/2004 | Ghinelli |
| 2004/0093046 A1 | 5/2004 | Sand |
| 2005/0079147 A1 | 4/2005 | Delaey |
| 2006/0172944 A1* | 8/2006 | Wiegand .............. A61K 9/0048 514/8.1 |
| 2008/0064098 A1 | 3/2008 | Allickson |
| 2008/0181935 A1 | 7/2008 | Bhatia |
| 2008/0181967 A1 | 7/2008 | Liu |
| 2008/0286378 A1 | 11/2008 | Behrens |
| 2009/0054350 A1 | 2/2009 | Tayot |
| 2010/0318048 A1 | 12/2010 | Hoefinghoff |
| 2011/0269667 A1 | 11/2011 | Shoseyov |
| 2012/0010727 A1 | 1/2012 | Young |
| 2013/0045927 A1 | 2/2013 | Dana ..................... A61K 38/13 514/20.8 |
| 2014/0336600 A1 | 11/2014 | Harrell |
| 2015/0025366 A1 | 1/2015 | Harrell |

FOREIGN PATENT DOCUMENTS

| | | |
|---|---|---|
| WO | 2004026244 | 1/2004 |
| WO | 2006091546 | 8/2006 |
| WO | 2015134936 | 9/2015 |

OTHER PUBLICATIONS

"What is Sterilizing Filtration and Why is it important?" Bioprocess Pharmaceutical Filtration Team, 2015, retrieved from URL: http://blog.parker.com/what-is-sterilizing-filtration-and-why-is-it-important (Year: 2015).*
U.S. Appl. No. 15/053,497, filed Feb. 25, 2016, Harrell.
Adzick, et al., "Cells, matrix, growth factors, and the surgeon. The biology of scarless fetal wound repair", Ann Surg, 220:10 8 (1994).
Ainslie, "Inhalational injuries produced by smoke and nitrogen dioxide", G, Respir Med. 87(3):169-74(1993).
Anker, et al., "Amniotic fluid as a novel source of mesenchymal stem cells for therapeutic transplantation", Blood, 102:1548 9 (2003).
Baur, et al., "Output and aerosol properties of 5 nebulizer/compressor systems with arformoterol inhalation solution", Respiratory Care, 54(10:1342-7 (2009).
Bergeron,et al.,"Airway remodeling in asthima: from benchside to clinical practice", Can Respir J., 17(4): e85-e93 (2010).
BIOSIS Database accession No. PREV200510252583, "Tropical application of amniotic fluid reduces corneal neovascularization after ocular alkali burn" ,1 page, appeared Apr. 1, 2004, retrieved Jul. 28, 2009.

(Continued)

*Primary Examiner* — Allison M Fox
(74) *Attorney, Agent, or Firm* — Fresh IP PLC; Michael Anderson; Aubrey Y. Chen

(57) ABSTRACT

A human amniotic fluid formulation has been developed for topical application to the eye, which is useful for the treatment of ocular diseases and injuries including dry eyes, Sjogren's Syndrome, cataracts, burns and injuries to the eye tissues. The formulation is a sterile de-cellularized human amniotic fluid (D-HAF), devoid of amniotic stem cells and elements of micronized membrane or chorion particles. Methods for treating, or preventing various ocular diseases, injuries and disorders using the formulation, optionally in combination with one or more therapeutic, prophylactic or diagnostic agents are described.

14 Claims, No Drawings

(56) References Cited

OTHER PUBLICATIONS

Castro-Combs, et al., "Cornel wound healing is modulated by topical application of amniotic fluid in an exvivo organ culture model", Exp Eye Res., 87:56-63 (2008).
D'Agostino, et al., "Mesenchymal stem cell therapy for the treatment of chronic obstructive pulmonary disease", Expert Opin Biol Ther. 10(5):681-7 (2010).
Dua, et al., "A new classification of ocular surface burn", Br J Ophthalmol, 85:1379-83 (2001).
Duffy, et al., "Vascular Endothelial Growth Factor (VEGF) and Its Role in Non-Endothelial Cells: Autocrine Signalling by VEGF", In: Madame Curie Bioscience Database [Internet]. Austin (TX): Landes Bioscience (2000).
Fletcher, et al., "The natural history of chronic airflow obstruction", Br Med J. 1:1645-8 (1977).
Gao, et al., "Effects of amniotic fluid on proteases: a possible role of amniotic fluid in fetal wound healin", Ann Plastic Surg, 33:128 34 (1994).
Gorguner, et al., "Acute inhalation injury", Eurasian J Med. 42(1):28-35(2010).
GU,et al., "Mesenchymal stem cells alleviate airway inflammation and emphysema in COPD through down-regulation of cyclooxygenase-2 via p38 and ERK MARk pathways", Sci Rep. 5:8733 (2015).
Hartzell, "Overview of combustion toxicology", Toxicology.,115(1-3):7-23 (1996).
Herretes, et al., "Use of topical human amniotic fluid in the treatment of acute ocular alkali injuries in mice", Am J Ophthalmology, 142(2):271-8 (2006).
Hoeben, et al., "Vascular endothelial growth factor and angiogenesis", Pharmacol Rev, 56:549-80 (2004).
Hoyert, et al., "Deaths: preliminary data for 2011". Natl Vital Stat Rep. 61(6):1-65 (2012).
International Search Report and Written Opinion for PCT/US206/056231 dated Dec. 6, 2016.
International Search Report and Written Opinion for PCT/US206/056267 dated Dec. 7, 2016.
Kales, et al., "Acute chemical emergencies", N Engl J Med., 19; 350(8):800-8 (2004).
Karacal, et al., "Effe t of human amniotic fluid on bone healing", J Surg Res., 129(2):283-7 (2005).
Lee, et al, "Effect of amniotic fluid in corneal sensitivity and nerve regeneration after excimer laser ablation", Cornea, 15(5):517-24 (1996).
Maraldi, et al., "Role of hepatocyte growth factor in the immunomodulation potential of amniotic fluid stem cells", Stem Cells Transl Med, 4(6):539-47 (2015).
Nagase, et al., "Structure and function of matrix metalloproteinases and TIMPs", Cardiovasc Res., 69(3): 562-73 (2006).
Nemery, "Metal toxicity and the respiratory tract", Eur Respir J. 3(2):202-19 (1990).
Newman, et al., "Occupational illness", N Engl J Med. 26; 333(17):1128-34 (1995).
Ozgenel, et al., "Effect of human amniotic fluid on peritendinous adhesion formation and tendon healing after flexor tendon surgery in rabits", J Hand Surg., 26(2):332-9 (2001).
Ozgenel, et al., "Effects of human amniotic fluid on cartilage regeneration from free perichondrial grafts in rabits", British J Plastic Surg., 57(5):423-8 (2004).
Ozgenel, et al., "Effects of human amniotic fluid on peripheral nerve scarring and regeneration in rats", J Neurosurg, 98:371 7 (2003).
Sporn, et al., "Transforming growth factor-beta: biological function and chemical structure", Science, 233(4763) 532-4 (1986).
Todderud, et al., "Epidermal growth factor: the receptor and its function", Biofactors., 2(1):11-5 (1989).
Weiss, et al., "placebo-controlled, randomized trial of mesenchymal stem cells in COPD", Chest. 143(6):1590-8 (2013).
Woode, et al., "Collagenolytic matrix metalloproteinases in chronic obstructive lung disease and cancer", Cancers, 7(1): 329-341 (2015).
Yun, et al., "Fibroblast growth factors: biology, function, and application for tissue regeneration", J Tissue Eng, 218142. doi:1-18 (2010).

* cited by examiner

AMNIOTIC FLUID TOPICAL FORMULATION

CROSS-REFERENCE TO RELATED APPLICATIONS

This application claims benefit of U.S. Provisional Application No. 62/239,677, filed Oct. 9, 2015, which is incorporated by reference in its entirety.

STATEMENT REGARDING FEDERALLY SPONSORED RESEARCH

This application is a continuation of pending U.S. Ser. No. 15/289,632, filed Oct. 10, 2016, which claims benefit of and priority to U.S. Provisional Application No. 62/239,677, filed Oct. 9, 2015, which are incorporated by reference in their entirety.

FIELD OF THE INVENTION

The invention largely relates to the management of a diverse number of ophthalmic diseases, injuries and disorders (e.g., dry eye syndrome, chronic redness, ocular burns, cataract suppression and Sjogren's Syndrome) with a human amniotic fluid ocular formulation.

BACKGROUND OF THE INVENTION

Diminished vision has a direct causal impact on a person's ability to perform basic functions such as walking, reading, driving and other common activities. Good ocular health contributes significantly to a person's quality of life and their ability to perform common daily activities and simple functions in their routine environments. Disorders and diseases of the eyes can be severely incapacitating, and occur in a wide variety of forms. Millions of people suffer from some form of visual impairment.

As an example, dry eye, a common ocular disorder sometimes related to autoimmune disorders, the formation of cataracts and aging in general, afflicts tens of millions of people globally. The lives of people with dry eye are negatively impacted due to consistent pain, redness and/or dryness of the eyes. Presently, a mixture of artificial tears (AT) OTC eye drops are used for soothing eye irritation and lubricating the eyes. Most provide minimal relief for limited durations and require several daily reapplications. These contribute varying stages of relief with no capacity to modify the disease. Human amniotic membrane (HAM) has been used efficaciously to treat specific eye surface injuries and maladies. However, the use of HAM often involves the skills of a physician and additional expense to patients. Additionally, these procedures usually impose severe vision impairment during treatment as the amniotic membrane is non-transparent. Ultimately, the benefits of the procedure last only as long as the membrane is in place, so the procedure is not particularly useful for chronic conditions such as dry eye.

It is an object of the present invention to provide a formulation that can be used for the management of various ocular diseases, injuries and disorders, and that is affordable, readily accessible and easy to use for both clinician and patient.

SUMMARY OF THE INVENTION

A human amniotic fluid formulation and method of use thereof have been developed for topical application to the eye for the treatment of ocular diseases and injuries including dry eyes, Sjogren's Syndrome, cataracts, burns and injuries to the eye tissues. A specifically formulated sterile filtered de-cellularized human amniotic fluid that has not been heat treated or treated with ethidium bromide is applied directly to the eye(s), preferably as a liquid ocular solution, much like a common liquid eye drops, lubricant or gel. The formulation can alleviate or prevent at least one symptom of a number of ocular injuries and diseases, including chronic dry eye disease, Sjogren's syndrome, and burns or injuries, corneal neovascular disorders, corneal opacities (including corneal haze), prolonged redness and inflammation of the eye(s).

The formulation is a sterile de-cellularized human amniotic fluid (D-HAF), preferably diluted with a pharmaceutically accepted carrier, and typically administered using a standard eye dropper apparatus. D-HAF contains over 300 human growth factors. D-HAF is devoid of amniotic stem cells and elements of micronized membrane or chorion particles. The dilution ratio of the D-HAF is dependent on the severity of the disorder or injury. For example, early to moderate dry eye or chronic redness, surface inflammation and, intraocular inflammation may be best treated with a low concentration, whereas Sjogren's Syndrome, severe Dry Eye, a corneal neovascular disorder, or corneal opacity will typically utilize a higher concentration of D-HAF. Daily applications of D-HAF deliver a sustainable level of beneficial growth factors.

D-HAF is prepared from human amniotic fluid from which the amniotic stem cells and particulate matter have been removed. In the preferred embodiment, the process consists of separating the cells from the AF using centrifugation and utilizing a series of filtration devices to remove all remaining cells and bioburden. Each lot is tested for bioburden and is certified sterile to contain <1 harmful organisms. The purified fluid is sterilized without the use of harsh terminal irradiation, e-beam or Ethylene Oxide (EO).

Methods for treating or preventing an ocular disease, disorder, or injury of the eye using the described formulation are described. In some embodiments, the formulation is administered with a pharmaceutically acceptable carrier. In some embodiments, the formulation is administered as a solution, suspension, ointment, or gel, with or without an implant. In some embodiments, the disorders associated with the eye that are suitable for treatment include dry eye disease, ocular burns, tears or injury to the eye or associated structures, corneal neovascular disorders, corneal opacities (including corneal haze), ocular blast injuries, eye infections, eye surgeries, drug-induced eye conditions, and prolonged redness and inflammation of the eye. In some embodiments, the disorders to be treated using the D-HAF are amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), panuveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof. Other disorders including injury, burn, or abrasion of the cornea, cataracts and age related degeneration of the eye or vision associated therewith.

Methods for treating, or preventing a disease, disorder, or injury of the eye using the described formulation in combination with one or more therapeutic, prophylactic or diagnostic agents are also described. In some embodiments, the D-HAF is administered prior to, in conjunction with, subsequent to, or alternation with treatment with one or more therapeutic, prophylactic or diagnostic agents. In some embodiments, the one or more therapeutic, prophylactic or diagnostic agents are selected from the group consisting of an anti-glaucoma agent, an anti-angiogenesis agent, an anti-infective agent, an anti-inflammatory agent, an analgesic agent, a local anesthetic, a growth factor, an immunosuppressant agent, an anti-allergic agent, an anti-oxidant, and a cytokine. In some embodiments, the one or more diagnostic agents include paramagnetic molecules, fluorescent compounds, magnetic molecules, and radionuclides, x-ray imaging agents, and contrast media.

DETAILED DESCRIPTION OF THE INVENTION

I. Definitions

"Active Agent," as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder. "Ophthalmic Drug" or "Ophthalmic Active Agent", as used herein, refers to an agent that is administered to a patient to alleviate, delay onset of, or prevent one or more symptoms of a disease or disorder of the eye, or diagnostic agent useful for imaging or otherwise assessing the eye.

"Effective amount" or "therapeutically effective amount," as used herein, refers to an amount effective to alleviate, delay onset of, or prevent one or more symptoms, particularly of a disease or disorder of the eye.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

"Nanoparticle," as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle," as used herein, generally refers to a particle having a diameter, such as an average diameter, from about 1 micron to about 100 microns, preferably from about 1 micron to about 50 microns, more preferably from about 1 to about 30 microns. The microparticles can have any shape. Microparticles having a spherical shape are generally referred to as "microspheres".

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Pharmaceutically Acceptable," as used herein, refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Implant," as generally used herein, refers to a polymeric device or element that is structured, sized, or otherwise configured to be implanted, preferably by injection or surgical implantation, in a specific region of the body so as to provide therapeutic benefit by releasing one or more therapeutic, prophylactic or diagnostic agents over an extended period of time at the site of implantation. For example, intraocular implants are polymeric devices or elements that are structured, sized, or otherwise configured to be placed in the eye, preferably by injection or surgical implantation, and to treat one or more diseases or disorders of the eye by releasing one or more therapeutic, prophylactic or diagnostic agents over an extended period. Intraocular implants are generally biocompatible with physiological conditions of an eye and do not cause adverse side effects. Generally, intraocular implants may be placed in an eye without disrupting vision of the eye.

II. Compositions

Formulations of purified human amniotic fluid are provided. Typically, the formulations include sterile de-cellularized human amniotic fluid (D-HAF), either in fluid form or solid form, for example, lyophilized powder, alone or in combination with appropriate excipients. Other active agents can be included. D-HAF contains over 300 human growth factors. D-HAF is devoid of amniotic stem cells and elements of micronized membrane or chorion particles.

A. Purified Amniotic Fluid Formulation

Amniotic fluid ("AF") contains nutrients and growth factors that facilitate fetal growth, provides mechanical cushioning and antimicrobial effectors that protect the fetus, and allows assessment of fetal maturity and disease. AF typically contains mixtures of growth factors, pro-inflammatory cytokines and anti-inflammatory cytokines, as well as a variety of macromolecules including carbohydrates, proteins and peptides such as enzymes and hormones, lipids, lactate, pyruvate, and electrolytes.

In some embodiments, the raw fluid directly collected from the source is not heat-treated, chemical-treated, or fractionated to produce the disclosed formulations. In some embodiments, the formulation retains more than 50%, more than 60%, more than 70%, more than 80%, or preferably more than 90%, of the total amniotic factors present in the raw fluid. In some embodiments, the formulations are not diluted with any additional solution for storage. In some embodiments, the formulations are diluted prior to application to the eyes. In some embodiments, the formulations are not concentrated relative to the raw fluid.

In some embodiments, the formulation is a diluted sterile de-cellularized human amniotic fluid (D-HAF), which preferably has not been heat treated nor sterilized with ethidium bromide, typically administered using a standard eye dropper apparatus. D-HAF contains over 300 human growth factors. D-HAF is devoid of cells, including amniotic stem cells, and elements of micronized membrane or chorion particles. The purified fluid is sterilized without the use of harsh terminal irradiation, e-beam or Ethylene Oxide (EO). In the preferred embodiment, the process consists of separating the cells from the AF using centrifugation and utilizing a series of filtration devices to remove all remaining cells and bioburden. Each lot is tested for bioburden and is certified sterile to contain <1 harmful organisms.

Generally, methods of preparing sterile de-cellularized amniotic fluids involve a series of centrifugation and filtration steps. Preferred methods of preparing sterile de-cellularized amniotic fluid are described in detail in U.S. application Ser. No. 15/053,497.

1. Method of Preparation

In some embodiments, the formulation is prepared from sterile human amniotic fluid obtained from a woman, removing cells, large particles and other undissolvables are removed, preferably by high speed centrifugation to obtain clarified amniotic fluid, the clarified amniotic fluid filtered through filters having a pore size of about 5 µm to about 10 µm to obtain a micron filtrate, filtering the micron filtrate through filters with a pore size of about 1.0 µm to obtain a second filtrate, filtering the filtrate through submicron filters with the pore size of 0.45 µm or/and 0.2 µm to obtain the sterilely filtered amniotic fluid.

In some embodiments, a collection procedure is performed in a sterile operating room environment during an elective C-section. Typically, the woman is undergoing a pre-caesarian surgical procedure. The steps of obtaining the sterile human amniotic fluid includes the steps of turning on a ultrasound device to provide guidance for the process of obtaining human fluid from the woman, inserting a blunt tip needle into the amniotic sac of the woman, attaching the blunt tip needle to a three-way stopcock, connecting a Luer lock syringe to the three-way stopcock, connecting a first end of a length of sterile tubing with the three-way stopcock, and collecting sterilely the amniotic fluid through the blunt tip needle and sterile tubing into a collection container.

In this embodiment, the sterile collection container includes a pump with a suction device. The suction device is a low suction device or a spring loaded low suction device. The suction device is fluidly connected to an internal balloon. This embodiment further includes manually pumping up the internal balloon in the sterile collection container using the low suction device to allow a low-level suction and collection of the amniotic fluid.

In some embodiments, the step of removing cells, large particles and other undissolvables from the human amniotic fluid includes a first step of centrifuging or depth filtering the human amniotic fluid. In some embodiments, the human amniotic fluid is centrifuged at about 5,000 rpm to about 10,000 rpm for about 30 minutes to about 60 minutes. In this embodiment, filters of about 5 µm to about 10 µm are used for the first. These can be cellulose ester filters, glass fiber filters, nylon capsule filters or nylon cartridge filters. The filters with the pore size of 1.0 µm are capsule filters or cartridge filters. The filters with the pore size of 1.0 µm are poly ether sulfone, poly vinylidene fluoride or cellulose acetate membrane filters. The filters with the pore size of 0.45 µm or 0.2 µm are capsule filters or cartridge filters. The filters with the pore size of 0.45 µm or 0.2 µm are poly ether sulfone membrane filters, poly vinylidene fluoride or cellulose acetate membrane filters.

The sterilely filtered human amniotic fluid contains growth factors including human growth hormone, transforming growth factor beta 1, vascular endothelial growth factor, epidermal growth factor, transforming growth factor beta 3, and growth differentiation factor 11 or combinations thereof.

In some embodiments, the process of obtaining the sterile amniotic fluid further includes the step of lyophilizing the sterile amniotic fluid to obtain a lyophilisate. The lyophilisate can be further sterilized by e-beam irradiation or gamma ray irradiation to reinforce the sterility.

Tools to obtain sterilely filtered human amniotic fluid from a woman, include a three-way stopcock, a sterile blunt tip needle aseptically attached to the three-way stopcock, a Luer lock syringe aseptically connected to the three-way stopcock, a sterile tubing aseptically connected to the three-way stopcock, a collection container or a collection container including a pump with suction device connected with the sterile tubing, a set of filters having the pore size of about 5 µm to about 10 µm, a set of capsule or cartridge filters having the pore size of about 1 µm, a set of capsule or cartridge filters having the pore size of about 0.45 µm or 0.2 µm, a set of sterile syringes or vials to store the sterile filtered amniotic fluid and operating instructions on using the kit to obtain sterilely filtered human amniotic fluid. The filters having the pore size of from about 5 µm to about 10 µm and the capsule or cartridge filters are made from cellulose ester, glass fiber or nylon.

The sterile collection container may include a pump with a suction device. The suction device may be a low suction device or spring loaded low suction device. In another aspect the suction device may be fluidly connected to an internal balloon. Further to this aspect the method includes manually pumping up the internal balloon in the sterile collection container using the low suction device to allow a low-level suction and collection of the amniotic fluid. In yet another aspect the sterile collection container may include an inlet. Further to this particular aspect the method includes connecting a second end of the tubing to the inlet of the sterile collection container. The sterile collection container may include a vent having a cap.

In some embodiments, utilizing the incision site immediately prior to performing the C-section and with ultrasound guidance to protect the fetus and mother provides a minimal or no risk environment for collection. Collection is achieved via a low level suction established within a collection container and/or via gravity. Typically, after high speed centrifugation, filtration with 5 to 10 µm filters (low protein binding filter) is used to complete the removal of cells and large particles. Submicron filtration is then conducted with 1 μm and 0.45 μm or/and 0.2 μm filters (low protein binding filter), two in a series connection, to remove gross contaminates. Under this condition, soluble growth factors will pass through this filter to achieve a semi-sterile condition, very low bioburden counts. If under a strict aseptic operation condition, a $10^{-3}$ sterility assurance level is achieved. A $10^{-6}$ sterility assurance level can be achieved by submicron filtration with a 0.22 μm filter (low protein binding filter) at the end and sterile packaging to achieve a sterile product. One can monitor the filtrate after each filtration step to determine which components are removed and then to determine which process to use to achieve the desirable product.

One may use membrane filters including or made of hydrophilic polyethersulphone (PES) to filter protein solutions. Filter disks for small volumes and different sizes of cartridges for larger volumes such as 1 liter and more are used. Hydrophobic membranes like PTFE which are designed for liquids devoid of proteins should not be used. Start with centrifugation at 5000 to 8000 rpm for at least 30 minutes. Next, the supernatant is filtered with a prefilter to remove residual protein aggregates and precipitates in suspension (AP20 can be used). If one directly uses a 0.6/0.2 μm filter, after prefiltration, one may experience slow filtration rates and the flow may stop too quickly. It may be desirable to make intermediate filtration steps using 1.2 μm and 0.8 μm membranes. Typically, a final filtration through 0.2 μm is necessary to get the best sterility assurance level and produce a sterile amniotic fluid for injections. The final filtrate can be stored in frozen condition at about −20° C. to about −80° C. for long term storage. In addition, the sterilely filtered amniotic fluid may be distributed in vials equipped with special rubber stoppers for sterile lyophilisation.

The sterile amniotic fluid can be lyophilized to yield a lyophilisate. The sterilely filtered amniotic fluid may be distributed in vials equipped with special rubber stoppers for sterile lyophilisation. The lyophilisation is carried out in a sterile environment. The rubber stoppers on the vials are then automatically pushed down in the freeze dryer to definitively close them. Finally an aluminum cap is sealed on each vial to protect its sterile content. In such a lyophilized state, the amniotic fluid may be stored at +4° C. or room temperature for at least one year without decrease of its biological activity. The lyophilisate can be irradiated by e-beam irradiation or gamma ray irradiation to insure the sterility. For its medical use, the sterile amniotic fluid may be reconstituted by adding the initial volume of sterile water to the powder in order to restore a transparent and homogeneous physiological liquid.

2. Sources of Amniotic Fluid Formulations

In some embodiments, the amniotic fluid formulations are prepared from sterile human amniotic fluid obtained from a pregnant woman. Suitable sources, e.g. of human AF, include AF that is obtained from patients who are undergoing amniocentesis, patients who are undergoing a Caesarean section delivery and patients undergoing normal delivery using a specially designed receptacle to collect the fluid after rupture of membranes.

The de-cellularized human amniotic fluid (D-HAF) formulations can be stored for long periods of time, allowing for a broad range of application methods, including distribution and storage as aerosols, solutions, powders, etc. In some embodiments, the sterile D-HAF is refrigerated at about 1° C. to about 10° C. for long-term storage. In a further embodiment, the sterile D-HAF is refrigerated at 4° C. for up to 12 months and more. Preferably, the long-term storage does not reduce the quantity of the total soluble proteins or factors present in the D-HAF. For some embodiments, the total soluble proteins retained after long-term storage in refrigerated conditions is about 10%, 20%, 30%, 40%, 50%, 60%, 70%, 80%, or 90% of the fresh D-HAF. D-HAF formulations containing amniotic factors can be supplied as a clear one-part solution in a suitable container for storage at 4° C., or for storage at −20° C., or at −80° C. For example, liquid formulations in prefilled aliquots can be suitable for storage at 1-5° C., or for storage at −20° C., or at −80° C. The liquid formulation can be suitable for topical application in a nebulizer or an spray. In other embodiments, the fluid can be supplied as a kit that can be stored at 4° C., at −20° C., or at −80° C. until needed.

In some embodiments, D-HAF formulations use a final filtration through 0.2 μm to produce a sterile amniotic fluid without any irradiation. In some embodiments, D-HAF formulations have all) $10^{-6}$ sterility assurance level without irradiation. In other embodiments, lyophilisate derived from amniotic fluid through lyophilisation may be irradiated by e-beam irradiation or gamma ray irradiation to add another guarantee for the final sterility of the powder.

3. Growth Factors, Cytokines and Other Molecules

Growth factors and their receptors control a wide range of biological functions, regulating cellular proliferation, survival, migration and differentiation. Growth factors found in AF play a critical role in fetal growth and development.

A non-limiting list of growth factors that have been identified in AF includes such as epidermal growth factor (EGF), insulin-like growth factor I (IGF-I), vascular endothelial growth factor A (VEGF-α), tumor necrosis factor A (TNF-α), hepatocyte growth factor (HGF), fibroblast growth factor 7 (FGF7), matrix metallopeptidase (MMP-9), granulocyte-colony stimulating factor (GCSF), matrix metalloproteinase-7 (MMP-7), matrix metalloproteinase-7 (MMP-13), transforming growth factor alpha (TGF-α), transforming growth factor beta (TGF-β), fibroblast growth factor 4 (FGF-4), endocrine gland-derived vascular endothelial growth factor (EG-VEGF), interleukin 8 (IL-8), fibroblast growth factor 21 (FGF-21), angiopoietin-2 (ANG2), Glial cell-derived neurotrophic factor (GDNF), fibroblast growth factor 19 (FGF-19), TIMP metallopeptidase inhibitor 2 (TIMP-2), angiopoietin-1 (ANG-1), Transforming growth factor beta 1 (TGFβ1), macrophage colony-stimulating factor (M-CSF), angiotensinogen, platelet derived growth factor-AA (PDGF-AA), and stem cell factor (SCF).

Epidermal growth factor (EGF) is a small polypeptide hormone with mitogenic properties in vivo and in vitro. EGF elicits biologic responses by binding to a cell surface receptor which is a transmembrane glycoprotein containing a cytoplasmic protein tyrosine kinase. EGF responses are mediated by ligand binding and activation of this intrinsic protein kinase. The receptor can be phosphorylated by other protein kinases, and this may regulate receptor function. Stimulation of the receptor tyrosine kinase activity by ligand binding must regulate the activity of an as yet undefined molecule(s) responsible for transmitting a mitogenic signal to the nucleus (Todderud G, et al., Biofactors. 1989, 2(1): 11-5).

Vascular endothelial growth factor (VEGF), also known as vascular permeability factor (VPF), was originally described as an endothelial cell-specific mitogen. VEGF is produced by many cell types including tumor cells, macrophages, platelets, keratinocytes, and renal mesangial cells. The activities of VEGF are not limited to the vascular system; VEGF plays a role in normal physiological functions such as bone formation, hematopoiesis, wound healing, and development (Duffy A M et al., In: Madame Curie Bioscience Database [Internet]. Austin (Tex.): Landes Bioscience (2000)).

TGF-α has a structure similar to EGF and binds to the same receptor. The amnion cells of the umbilical cord express EGF, TGF-α, and the functional EGF/TGF-α receptor, suggesting the possibility of a regulating role of the amnion in fetal growth and development. EGF and TGF-α have also been shown to stimulate the production of surfactant components. TGFβ1 is believed to induce terminal differentiation of intestinal epithelial cells and to accelerate the rate of healing of intestinal wounds by stimulating cell migration. TGFβ1 may also stimulate IgA production. VEGF-A is a signal protein that stimulates vasculogenesis and angiogenesis (Hoeben Am, et al., *Pharmacol Rev* 2004, 56:549-580).

Transforming growth factor-beta (TGF-β) is a multifunctional peptide that controls proliferation, differentiation, and other functions in many cell types. Many cells synthesize TGF-beta and essentially all of them have specific receptors for this peptide. TGF-beta regulates the actions of many other peptide growth factors and determines a positive or negative direction of their effects (Sporn M B, et al., Science 1986, 233(4763) 532-534).

Hepatocyte growth factor (HGF), the ligand for the receptor tyrosine kinase encoded by the c-Met proto-oncogene, is a multidomain protein structurally related to the pro-enzyme plasminogen and with major roles in development, tissue regeneration and cancer. A recent study showed its immunomodulation potential of amniotic fluid stem cells (Maraldi T, et al. *Stem Cells Transl Med,* 4(6):539-47 (2015)).

Fibroblast growth factors (FGFs) that signal through FGF receptors (FGFRs) regulate a broad spectrum of biological functions, including cellular proliferation, survival, migration, and differentiation. The FGF signal pathways are the RAS/MAP kinase pathway, PI3 kinase/AKT pathway, and PLCγ pathway, among which the RAS/MAP kinase pathway is known to be predominant. Several studies have recently implicated the in vitro biological functions of FGFs for tissue regeneration. Many current applications of FGF are in regeneration of tissues, including skin, blood vessel, muscle, adipose, tendon/ligament, cartilage, bone, tooth, and nerve tissues (Yun Y R, et al., J Tissue Eng 2010: 1(1)).

Matrix metalloproteinases (MMPs), also called matrixins, function in the extracellular environment of cells and degrade both matrix and non-matrix proteins. They play central roles in morphogenesis, wound healing, tissue repair and remodeling in response to injury, e.g. after myocardial infarction, and in progression of diseases such as atheroma, arthritis, cancer and chronic tissue ulcers. They are multi-domain proteins and their activities are regulated by tissue inhibitors of metalloproteinases (TIMPs) (Nagase H, et al., Cardiovascular Research, European Society of Cardiology, 562-573 (2006)).

Amniotic fluid also contains many pro- and anti-inflammatory cytokines. Pro- and anti-inflammatory cytokines play important immunoregulatory roles. Inflammation is characterized by interplay between pro- and anti-inflammatory cytokines. Cytokines are commonly classified in one or the other category: interleukin-1 (IL-1), tumor necrosis factor (TNF), gamma-interferon (IFN-gamma), IL-12, IL-18 and granulocyte-macrophage colony stimulating factor are well characterized as pro-inflammatory cytokines whereas IL4, IL-10, IL-13, IFN-alpha and transforming growth factor-beta are recognized as anti-inflammatory cytokines.

Exemplary pro-inflammatory cytokines include Eotaxin-2 (CCL24), interleukin 6 (IL-6), pulmonary and activation-regulated chemokine PARC or chemokine (C-C motif) ligand 18 (CCL18), total GRO which consisted of three subunits GROα/CXCL1, GROβ/CXCL2, and GROγ/CXCL3, expression of the neutrophil-activating CXC chemokine (ENA-78/CXCL-5), chemokine (C-C motif) ligand 21 (CCL21 or 6Ckine), macrophage inflammatory protein 3 alpha (MIP-3α or CCL20), monokine induced by gamma (MIG or CXCL-9), MIP-1α, chemokine (C-C motif) ligand 5 (CCL-5), also known as RANTES (regulated on activation, normal T cell expressed and secreted), Interleukin-1 alpha (IL-la), macrophage inflammatory protein-1β (MIP-1β or CCL4), tumor necrosis factor (TNFα) and monocyte chemotactic protein 2 (MCP-2 or CCL8).

Exemplary anti-inflammatory cytokines include the anti-inflammatory factors include interleukin 8 (IL-8), interleukin 13 (IL-13), interleukin 27 (IL-27), cytotoxic T-lymphocyte-associated protein 4 (CTLA-4), vascular endothelial growth factor D (VEGF-D), interleukin-1 receptor antagonist (IL-1Ra), transforming growth factor beta 1 (TGFβ1), interleukin 5 (IL-5) and interleukin 21 (IL-21).

B. Additional Therapeutic, Prophylactic or Diagnostic Agents

In some embodiments, sterile de-cellularized human amniotic fluid (D-HAF) are used in combination with one or more additional therapeutic, diagnostic, and/or prophylactic agents to alleviate discomfort, facilitate healing, and/or reduce or inhibit scarring. The active agents can be a small molecule active agent or a biomolecule, such as an enzyme or protein, polypeptide, or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be dispersed in, or otherwise associated with particles in the formulation. In certain embodiments, one or more additional active agents may also be dissolved or suspended in the pharmaceutically acceptable carrier.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

In the case of pharmaceutical compositions for the treatment of ocular diseases, the formulation may contain one or more ophthalmic drugs to treat, prevent or diagnose a disease or disorder of the eye. Non-limiting examples of ophthalmic drugs include anti-glaucoma agents, anti-angiogenesis agents, anti-infective agents, anti-inflammatory agents, an analgesic, a local anesthetic, growth factors, immunosuppressant agents, anti-allergic agents, an antioxidant, a cytokine, and combinations thereof.

The amount of a second therapeutic generally depends on the severity of the condition to be treated. Specific dosages can be readily determined by those of skill in the art. See Ansel, Howard C. et al. *Pharmaceutical Dosage Forms and Drug Delivery Systems* ($6^{th}$ ed.) Williams and Wilkins, Malvern, Pa. (1995). Alternatively, the sterile de-cellularized human amniotic fluid can be used in combination with cell delivery, for example, the delivery of stem cells, pluripotent cells, somatic cells, or combinations thereof.

In other embodiments, one or more therapeutic active agents such as an anti-glaucoma agent, an anti-angiogenesis agent, an anti-infective agent, an anti-inflammatory agent, an analgesic agent, a local anesthetic, a growth factor, an immunosuppressant agent, an anti-allergic agent, an antioxidant, and a cytokine are administered prior to, in conjunction with, subsequent to, or alternation with treatment with the de-cellularized human amniotic fluid of the disclosure.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic. In some cases, the active agent is an anti-allergic agent such as olopatadine and epinastine.

1. Anti-Glaucoma Agents

In some embodiments, the one or more additional active agent is one or more anti-glaucoma agents. Representative anti-glaucoma agents include prostaglandin analogs (such as travoprost, bimatoprost, and latanoprost), beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., parasympathomimetics, such as pilocarpine and ecothiopate), seretonergics muscarinics, dopaminergic agonists, and adrenergic agonists (such as apraclonidine and brimonidine).

2. Anti-Angiogenesis Agents

In some embodiments, the one or more additional active agent is one or more anti-angiogenesis agents. Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

3. Anti-Infective Agents

In some embodiments, the sterile de-cellularized human amniotic fluid is used in combination with one or more antimicrobial agents. An antimicrobial agent is a substance that kills or inhibits the growth of microbes such as bacteria, fungi, viruses, or parasites. Antimicrobial agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

Other exemplary antimicrobial agents include iodine, silver compounds, moxifloxacin, ciprofloxacin, levofloxacin, cefazolin, tigecycline, gentamycin, ceftazidime, ofloxacin, gatifloxacin, amphotericin, voriconazole, natamycin.

4. Local Anesthetics

In some embodiments, the disclosed compositions are used in combination with one or more local anesthetics. A local anesthetic is a substance that causes reversible local anesthesia and has the effect of loss of the sensation of pain. Non-limiting examples of local anesthetics include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and any combination thereof. In other aspects of this embodiment, the sterile DHAF composition comprises an anesthetic agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. The concentration of local anesthetics in the compositions can be therapeutically effective meaning the concentration is adequate to provide a therapeutic benefit without inflicting harm to the patient.

Ophthalmic anesthetics are agents that act locally to block pain signals at the nerve endings in the eyes. Some exemplary ophthalmic anesthetics are lidocaine, proparacaine, and tetracaine.

5. Anti-Inflammatory Agents

In some embodiments, the sterile de-cellularized human amniotic fluid is used in combination with one or more anti-inflammatory agents. Anti-inflammatory agents reduce inflammation and include steroidal and non-steroidal drugs. Suitable steroidal active agents include glucocorticoids, progestins, mineralocorticoids, and corticosteroids. Other exemplary anti-inflammatory agents include triamcinolone acetonide, fluocinolone acetonide, prednisolone, dexamethasone, loteprendol, fluorometholone, ibuprofen, aspirin, and naproxen. Exemplary immune-modulating drugs include cyclosporine, tacrolimus and rapamycin. Exemplary non-steroidal anti-inflammatory drug include ketorolac, nepafenac, and diclofenac.

In some embodiments, anti-inflammatory agents are anti-inflammatory cytokines. Exemplary cytokines are IL-10, TGF-$\beta$ and IL-35. Anti-inflammatory cytokines in the context of biomaterial implant, and tissue grafts are cytokine that induce an anti-inflammatory immune environment or suppress inflammatory immune environment. Activation of regulatory T cells, Tregs, is involved in the prevention of rejection, the induction and maintenance of peripheral tolerance of the allograft. Th17 cells are a subset of T helper cells which is characterized by the production of IL-17. Th17 cells have been suggested to play a role in allograft rejection. In some embodiments, cytokines to be added to the sterile DHAF compositions are those that induce Tregs activation (e.g. IL-25) and suppress Th17 activation (e.g. IL-10) for minimizing rejection.

6. Cofactors and Essential Nutrients

In some embodiments, the sterile de-cellularized human amniotic fluid composition further comprises one or more enzyme cofactors, and/or one or more essential nutrients. Exemplary cofactors include vitamin C, biotin, vitamin E, vitamin A, and vitamin K. Exemplary essential nutrients are amino acids, fatty acids, etc.

7. Cells and Tissues

In some embodiments, the sterile de-cellularized human amniotic fluid composition further comprises at least one eukaryotic cell type. Some exemplary eukaryotic cell types include stem cells, mesenchymal stem cells, immune cells such as T lymphocytes, B lymphocytes, natural killer cells, macrophages, dendritic cells, or combinations thereof.

C. Formulations

The sterile amniotic fluid formulation can be administered in concentrated form, diluted with sterile water or buffer, formulated as a gel, ointment, or suspension. It can include additional therapeutic, prophylactic or diagnostic agent, either in the solution, gel, ointment or suspension, or as particles (nanoparticles, liposomes, microparticles) or implants.

Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

1. Solutions, Gels, Ointments and Suspension

Numerous ophthalmological formulations are known and available. Solutions can be the sterile filtered amniotic fluid, concentrated or diluted with water, buffered saline, or an equivalent, formed into a gel with a polysaccharide such as alginate or hyaluronic acid, polyvinyl pyrrole, or ointment such as petrolatum or mineral oil, or emulsified with lipid or oil. Ophthalmic emulsions are generally dispersions of oily droplets in an aqueous phase. There should be no evidence of breaking or coalescence. Ophthalmic suspensions contain solid particles dispersed in a liquid vehicle; they must be homogeneous when shaken gently and remain sufficiently dispersed to enable the correct dose to be removed from the container. A sediment may occur, but this should disperse readily when the container is shaken, and the size of the dispersed particles should be controlled. The active ingredient and any other suspended material must be reduced to a particle size small enough to prevent irritation and damage to the cornea.

Ophthalmic ointments are sterile, homogeneous, semi-solid preparations intended for application to the conjunctiva or the eyelids. They are usually prepared from non-aqueous bases, e.g., soft paraffin (Vaseline), liquid paraffin, and wool fat. They may contain suitable additives, such as antimicrobial agents, antioxidants, and stabilizing agents.

When the solution is dispensed in a multidose container that is to be used over a period of time longer than 24 hours, a preservative must be added to ensure microbiologic safety over the period of use.

Ideally, the pH of ophthalmic drops should be equivalent to that of tear fluid, which is 7.4. However, the decision to add a buffering agent should be based on stability considerations. The pH selected should be the optimum for both stability of the active pharmaceutical ingredient and physiological tolerance. If a buffer system is used, it must not cause precipitation or deterioration of the active ingredient. The influence on the lachrymal flow should also be taken into account.

Although solutions with the same pH as lacrimal fluid (7.4) are ideal, the outer surfaces of the eye tolerate a larger range, 3.5 to 8.5. The normal useful range to prevent corneal damage is 6.5 to 8.5. The final pH of the solution is often a compromise, because many ophthalmic drugs have limited solubility and stability at the desired pH of 7.4. Buffers or pH adjusting agents or vehicles can be added to adjust and stabilize the pH at a desired level. Ophthalmic solutions are ordinarily buffered at the pH of maximum stability of the drug(s) they contain. The buffers are included to minimize any change in pH during the storage life of the drug; this can result from absorbed carbon dioxide from the air or from hydroxyl ions from a glass container. Changes in pH can affect the solubility and stability of drugs; consequently, it is important to minimize fluctuations in pH. The buffer system should be designed sufficient to maintain the pH throughout the expected shelf-life of the product, but with a low buffer capacity so that when the ophthalmic solution is instilled into the eye, the buffer system of the tears will rapidly bring the pH of the solution back to that of the tears. Low concentrations of buffer salts are used to prepare buffers of low buffer capacity.

The preparation of aqueous ophthalmic drops requires careful consideration of the need for isotonicity, a certain buffering capacity, the desired pH, the addition of antimicrobial agents and/or antioxidants, the use of viscosity-increasing agents, and the choice of appropriate packaging. Ophthalmic drops are considered isotonic when the tonicity is equal to that of a 0.9% solution of sodium chloride. The eye can usually tolerate solutions equivalent to 0.5-1.8% of sodium chloride.

Solutions that are isotonic with tears are preferred. An amount equivalent to 0.9% NaCl is ideal for comfort and should be used when possible. The eye can tolerate tonicities within the equivalent range of 0.6-2% NaCl without discomfort. There are times when hypertonic ophthalmic solutions are necessary therapeutically, or when the addition of an auxiliary agent required for reasons of stability supersedes the need for isotonicity. A hypotonic ophthalmic solution will require the addition of a substance (tonicity adjusting agent) to attain the proper tonicity range.

The most widely used ophthalmic buffer solutions are boric acid vehicle and Sorensen's modified phosphate buffer. The boric acid vehicle is a 1.9% solution of boric acid in purified water or preferably sterile water. It is isotonic with tears. It has a pH of approximately 5 and is useful when extemporaneously compounding ophthalmic solutions of drugs that are most stable at acid pH. This vehicle does not possess large buffer capacity, but it is sufficient to stabilize pH for the short expiratory periods used for compounded solutions, without overwhelming the natural buffers in lacrimal fluid. The second most commonly used buffer solution is the Sorensen's modified phosphate buffer and is used for drugs needing pH values between the range of 6.5-8.0. This buffer uses two stock solutions, one acidic containing $NaH_2PO_4$, and one basic containing $Na_2HPO_4$. The formulas for the stock solutions and their respective proportions used to obtain specific In some instances, the formulation is distributed or packaged in a liquid form. Alternatively, formulations for ocular administration can be packed as a solid, obtained, for example by lyophilisation of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

2. Particles and Implants Containing One or More Therapeutic, Prophylactic or Diagnostic Agents Dispersed in a Polymer Matrix Particles can also be formed containing one or more therapeutic, prophylactic or diagnostic agents dispersed or encapsulated in a polymeric matrix. The matrix can be formed of non-biodegradable or biodegradable matrices, although biodegradable matrices are preferred. The polymer is selected based on the time required for in vivo stability, i.e. that time required for distribution to the site where delivery is desired, and the time desired for delivery.

Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly (isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

Examples of preferred natural polymers include proteins such as albumin and prolamines, for example, zein, and polysaccharides such as alginate, cellulose and polyhydroxyalkanoates, for example, polyhydroxybutyrate.

The in vivo stability of the matrix can be adjusted during the production by using polymers such as polylactide co glycolide copolymerized with polyethylene glycol (PEG). PEG if exposed on the external surface may elongate the time these materials circulate since it is hydrophilic.

Examples of preferred non-biodegradable polymers include ethylene vinyl acetate, poly(meth)acrylic acid, polyamides, copolymers and mixtures thereof.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

Microparticle and nanoparticles can be formed using any suitable method for the formation of polymer micro- or nanoparticles known in the art. The method employed for particle formation will depend on a variety of factors, including the characteristics of the polymers present in the polymer-drug conjugate or polymer matrix, as well as the desired particle size and size distribution. The type of therapeutic, prophylactic or diagnostic agent(s) being incorporated in the particles may also be a factor as some therapeutic, prophylactic or diagnostic agents are unstable in the presence of certain solvents, in certain temperature ranges, and/or in certain pH ranges.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

Implants can be formed from one or more polymers. In preferred embodiments, the implants are intraocular implants. Suitable implants include, but are not limited to, rods, discs, wafers, and the like.

Implants can also be formed from a polymeric matrix having one or more therapeutic, prophylactic or diagnostic agents dispersed or encapsulated therein. The matrix can be formed of any of the non-biodegradable or biodegradable polymers described above, although biodegradable polymers are preferred. The composition of the polymer matrix is selected based on the time required for in vivo stability, i.e. that time required for distribution to the site where delivery is desired, and the time desired for delivery.

Implants can also be formed from blends of polymer-drug conjugates with one or more of the polymers described in Section B above.

The implants may be of any geometry such as fibers, sheets, films, microspheres, spheres, circular discs, rods, or plaques. Implant size is determined by factors such as toleration for the implant, location of the implant, size limitations in view of the proposed method of implant insertion, ease of handling, etc.

Where sheets or films are employed, the sheets or films will be in the range of at least about 0.5 mm×0.5 mm, usually about 3 to 10 mm×5 to 10 mm with a thickness of about 0.1 to 1.0 mm for ease of handling. Where fibers are employed, the fiber diameter will generally be in the range of about 0.05 to 3 mm and the fiber length will generally be in the range of about 0.5 to 10 mm.

The size and shape of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Intraocular implants may be spherical or non-spherical in shape. For spherical-shaped implants, the implant may have a largest dimension (e.g., diameter) between about 5 μm and about 2 mm, or between about 10 μm and about 1 mm for administration with a needle, greater than 1 mm, or greater than 2 mm, such as 3 mm or up to 10 mm, for administration by surgical implantation. If the implant is non-spherical, the implant may have the largest dimension or smallest dimension be from about 5 μm and about 2 mm, or between about 10 μm and about 1 mm for administration with a needle, greater than 1 mm, or greater than 2 mm, such as 3 mm or up to 10 mm, for administration by surgical implantation.

The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg. In some embodiments, the dimension are, or are similar to, implants already approved for intraocular injection via needle: diameter of 460 microns and a length of 6 mm and diameter of 370 microns and length of 3.5 mm.

Intraocular implants may also be designed to be least somewhat flexible so as to facilitate both insertion of the implant in the eye, such as in the vitreous, and subsequent accommodation of the implant. The total weight of the implant is usually about 250 to 5000 μg, more preferably about 500-1000 μg. In certain embodiments, the intraocular implant has a mass of about 500 μg, 750 μg, or 1000 μg.

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymer segments present in the implant, the properties of the one or more therapeutic, prophylactic or diagnostic agents present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymer segments and therapeutic, prophylactic or diagnostic agent are chosen so as to be stable at the temperatures required for manufacturing, usually at least about 85 degrees Celsius. However, depending on the nature of the polymeric components and the one or more therapeutic, prophylactic or diagnostic agents, extrusion methods can employ temperatures of about 25° C. to about 150° C., more preferably about 65° C. to about 130° C.

Implants may be coextruded in order to provide a coating covering all or part of the surface of the implant. Such coatings may be erodible or non-erodible, and may be impermeable, semi-permeable, or permeable to the Therapeutic, prophylactic or diagnostic agent, water, or combinations thereof. Such coatings can be used to further control release of the therapeutic, prophylactic or diagnostic agent from the implant.

Compression methods may be used to make the implants. Compression methods frequently yield implants with faster release rates than extrusion methods. Compression methods may employ pressures of about 50-150 psi, more preferably about 70-80 psi, even more preferably about 76 psi, and use temperatures of about 0° C. to about 115° C., more preferably about 25° C.

III. Methods of Administration

A. Disorders and Diseases to be Treated

The compositions and methods are suitable for any discomfort, pain, dryness, excessive tearing, injuries, infections, burns associated with the eye. In some embodiments, sterile de-cellularized human amniotic fluid (D-HAF) formulations are used to alleviate pain, facilitate healing, and/or reduce or inhibit scarring.

The compositions and methods are also suitable for prophylactic uses. In some embodiments, sterile de-cellularized human amniotic fluid (D-HAF) formulations are used to relieve discomfort associated with extended computer use in human subjects.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, meibomian gland dysfunction, anterior and posterior blepharitis, conjunctival hyperemia, conjunctival necrosis, cicatrical scaring and fibrosis, punctate epithelial keratopathy, filamentary keratitis, corneal erosions, thinning, ulcerations and perforations, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age-related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof. Other disorders including injury, burn, or abrasion of the cornea, cataracts and age related degeneration of the eye or vision associated therewith.

In some embodiments, the disclosed formulations applied to the eye dissolve cataracts, reducing cataracts about 5%, about 10%, about 20%, about 30%, about 40%, about 50%, about 60%, about 70%, about 80%, about 90%, or more than 90%, in size. In other embodiments, the disclosed formulations dissolve cataracts, eliminating the need for an operation to remove cataracts. In some embodiments, the formulations are used to assist recovery from a cataract removal procedure.

The formulations may be administered to animals, especially mammalian animals for treating or alleviating pain, disease, disorder, infection, or injury of the eye. Mammalian subjects, include, but are not limited to, humans, primates such as monkeys and apes, canines such as dogs, felines such as cats, bovines such as cows, equines such as horses, swine such as pigs, and rodents such as mice and rats. In some embodiments, the formulations are used to relieve/treat dry eye, treat eye infection, improve vision, or assist recovery from a surgical procedure on the eye in mammals such as dogs, cats, rabbits, and horses.

Case studies have shown an immediate positive disease modification for patients with mild to moderate and severe dry eye syndrome, glaucoma, Sjogren's syndrome, possible Ankylosing spondylitis and age-related declining vision. Due to the viscosity of D-HAF, drops applied directly onto the eye adhere to the ocular surface longer than common over the counter ("OTC") artificial tear formulas. The capacity to adhere to the ocular surface is paramount when treating injuries and diseases such as Sjogrens Syndrome and chemical burns. Some unexpected results reported in the study were perceptible improvement to clarity of vision which had been diminished in several patients. Relief from varying levels of ocular discomfort or pain was observed. Nine (9) patients were administered Snell Eye Chart exams at the start and completion of the initial 30 day study of the D-HAF therapy. Five (5) of the nine demonstrated enriched visual acuity and consistently conveyed improvements in visual clarity, distance and reading ability. Improvements of one to several lines on the test charts were recorded. Only two patients tested at undetectable improvement levels. Visual acuity appeared to be correlated to the level of corneal integrity of the recipient. This was an unexpected benefit from the D-HAF therapy and treatments. Other unexpected benefits were being able to read at night for the first time in years and regaining the visibility required to drive a car. Most participants were able to discontinue or drastically reduce the amount and frequency of using additional applications of artificial tears ("AT") drops and or alternate curatives. One participant diagnosed with mild dry eye exhibited no signs of the disease at the end of the initial 30 day trial.

1. Ocular Burns

In some embodiments, the formulations and methods described are used for assisting recovery from ocular burns, or from procedures managing ocular burns such as autolimbal or allolimbal transplantation.

Ocular burns such as thermal and chemical burns represent potentially blinding ocular injuries. Thermal burns result from accidents associated with firework explosions, steam, boiling water, or molten metal (commonly aluminum). Chemical burns may be caused by either alkaline or acidic agents.

Common alkaline agents include ammonium hydroxide used in fertilizer production, sodium hydroxide (caustic soda) used for cleaning drains and pipes, and calcium hydroxide found in lime plaster and cement. Alkaline agents are particularly damaging as they have both hydrophilic and lipophilic properties, which allow them to rapidly penetrate cell membranes and enter the anterior chamber. Alkali damage results from interaction of the hydroxyl ions causing saponification of cell membranes and cell death along with disruption of the extracellular matrix. Common acidic agents causing injury include sulphuric acid found in car batteries, sulphurous acid found in some bleaches, and hydrochloric acid used in swimming pools. Acids tend to cause less damage than alkalis as many corneal proteins bind acid and act as a chemical buffer. In addition, coagulated tissue acts as a barrier to further penetration of acid. Acid binds to collagen and causes fibril shrinkage.

Recovery of ocular surface burns depends upon the causative agent and the extent of damage to corneal, limbal, and conjunctival tissues at the time of injury. Damage to intraocular structures influences the final visual outcome. Thus, in some embodiments, the disclosed formulations are used to speed the recovery from an ocular burn.

2. Ocular Blast Injuries

Ocular blast injuries can be primary, from the blast wave itself; secondary, from fragments carried by the blast wind; tertiary, due to structural collapse or being thrown against a fixed object; or quaternary, from burns and indirect injuries. In some embodiments, the formulations are used in the management of injuries inflicted by blasts and explosions for preventative and/or therapeutic purposes.

3. Eye Surgery

The formulations are suitable for use in the management of eye surgeries. Eye surgery, ocular surgery, or ophthalmologic surgery, refers to any surgery that is performed on the eye or its adnexa. Exemplary ocular surgeries include laser eye surgery, cataract removal, glaucoma surgery such as canaloplasty, refractive surgery such as LASIK®, corneal surgery, vitreo-retinal surgery, eye muscle surgery, oculoplastic surgery such as eye lid surgery and orbital surgery, surgery involving the lacrimal apparatus, and eye removal.

In some embodiments, the formulations are used prior, during or after one or more ocular surgeries. Thus, in some embodiments, the formulations are used along with one or more systemic drugs. For example, D-HAF is applied as eye drops whilst the patient is on non-steroidal anti-inflammatory drugs such as ibuprofen.

In some embodiments, the formulations are used to assist recovery from an ocular surgery. In some embodiments, the formulations are used to prevent, reduce, or alleviate one or more symptoms from an ocular surgery. For example, the formulations can be used during recovery after a surgical procedure of amniotic membrane graft onto the ocular surface. In some embodiments, the formulations are used to prevent one or more potential complications from an ocular surgery such as an infection. In some embodiments, the formulations are used to assist local tissue repair, and/or minimize scarring of the surgical site.

4. Eye Infections

The formulations are suitable for use in the management of eye infections. Eye infections include infections from bacteria, fungi, and viruses. Eye infections can occur in different parts of the eye and can affect just one eye or both. Exemplary eye infections include conjunctivitis, stye, caratitis, and ocular herpes.

In some embodiments, the formulations are for prophylactic purposes to prevent an outset of a suspected eye infection. For example, if one person with an eye infection e.g., conjunctivitis, is identified, anyone who has been recently in contact with that person can use the disclosed formulation for prophylactic purposes. In some embodiments, the disclosed formulations are used to prevent, reduce, or alleviate one or more symptoms from an eye infection.

5. Drug-Induced Eye Conditions

The formulations are also suitable for use in the management of eye problems that arise as a side effect of using one or more systemic drugs. Thus, in some embodiments, the formulations are used prior, during or after taking one or more systemic drugs. Exemplary drugs that can cause ocular side effects include corticosteroids, antihistamines, antipsychotic medications, antimalarials, blood pressure medications, herbal medicines, erectile dysfunction drugs, anticholinergics, immunosuppressants, antibiotics, antiarrhythmic agents, and anti-cancer drugs/treatment. Some specific examples are bisphosphonate, amiodarone, tamsulosin, topiramate, ethambutol, minocycline, cyclosporine and tacrolimus.

Corticosteroids used for many conditions such as asthma, allergies, arthritis and skin conditions can cause swelling in the back of the eye or retina and potentially lead to cataracts. Antihistamines, used for conditions such as allergies, can raise certain patients' risk for glaucoma. Antipsychotic medications, such as THORAZINE® and MELLARIL® can be toxic to the retina. Antimalarials, such as PLAQUENIL® (hydroxychloroquine), used to treat malaria, lupus and rheumatoid arthritis, is a known retinal toxin, and the effects are irreversible. FOSAMAX®, a bisphosphonate that is prescribed for post-menopausal women to prevent calcium bone loss, can cause orbital inflammation, uveitis and scleritis.

Cyclosporine and Tacrolimus, commonly used in patients who have undergone organ or bone marrow transplants, can cause posterior reversible encephalopathy syndrome. These patients will present with bilateral vision loss. Minocycline is a tetracycline derivative and is commonly used to treat acne. Minocycline can cause increased intracranial pressure and papilledema, which can cause permanent vision loss if not reversed. Ethambutol is widely used to treat mycobacterial disease, including tuberculosis. If it is not taken at safe doses, it is an optic nerve toxin. Topiramate (Topamax) is used to treat epilepsy and migraine headaches, and it is used off-label for weight loss. It can cause angle-closure glaucoma soon after starting treatment. Tamsulosin (Flomax), which is used to treat prostate enlargement and improve urinary flow in men. The well-known syndrome, intraoperative floppy iris syndrome, used to occur only in men who were on medicine to relax their prostate. Women with these drugs can at the time of cataract surgery, make surgical risk much higher. Amiodarone (Cordarone) effectively treats cardiac arrhythmias. It causes the appearance of a whorl in the cornea, which does not usually cause symptoms, although some people can have a little bit of blurred vision.

Anticholinergics e.g., dicyclomine (BENTYL®), and other drugs with anticholinergic effects, are administered to patients who have stomach conditions that require stomach relaxers and to patients with Parkinson's disease. Young patients taking these drugs will develop difficulty with accommodation. Erectile dysfunction drugs, e.g., sildenafil citrate (VIAGRA®) and tadalafil (CIALIS®) are often prescribed for men with erectile dysfunction. Some of the ocular side effects include blue vision, and ischemic optic neuropathy. Blood Pressure Medications can cause glaucoma.

In some embodiments, the formulations and methods are used for treating, alleviating, and/or preventing one or more ocular symptoms that arise as a side effect from taking a systemic drug.

In some embodiments, the formulations and methods are used for treating, alleviating, and/or preventing one or more ocular symptoms in patients with ocular graft versus host disease. Ocular Graft Versus Host Disease (GVHD) occurs in patients who have undergone allogenic hematological stem cell transplantation. It can occur in patients who have acute or chronic GVHD, though it is more common in patients with the chronic form. Approximately 40-90% of patients with chronic GVHD will develop ocular symptoms. Exemplary ocular manifestations include moderate to severe keratoconjuncitvitis sicca, bilateral marginal keratitis, anterior uveitis, corneal ulceration or neovascularization. Thus, in some embodiments, the formulations are suitable for treating, alleviating, and/or preventing keratoconjuncitvitis sicca, bilateral marginal keratitis, anterior uveitis, corneal ulceration or neovascularization. In one embodiment, the formulations are used to improve vision of patients with ocular graft versus host disease after a bone marrow transplant for leukemia.

B. Dosages and Dosing Regimens

A human amniotic fluid formulation and method of use thereof have been developed for topical application to the eye, for the treatment of ocular diseases and injuries including dry eyes, Sjogren's Syndrome, cataracts, burns and injuries to the eye tissues. The method involves the management of a specifically formulated diluted sterile decellularized human amniotic fluid applied directly to the eye(s), preferably as a liquid ocular solution, much like a common liquid eye drops, lubricant or gel. The formulation delivered to the surface of the eye can alleviate or prevent at least one symptom of a number of ocular injuries and diseases, including in addition to chronic dry eye disease, Sjogren's syndrome, and burns or injuries, corneal neovascular disorders, corneal opacities (including corneal haze), prolonged redness and inflammation of the eye(s).

D-HAF has been tested and shown to contain over 300 human growth which can stimulate the proliferation of stem cells, thereby accelerating healing and contributing to modifying the advancement of disease. Due to the viscosity of D-HAF, drops applied directly onto the eye adhere to the ocular surface longer than common OTC artificial tear formulas. The capacity to adhere to the ocular surface is paramount when treating injuries and diseases such as Sjogrens Syndrome and chemical burns.

Unlike Human Amniotic Membrane treatments, in the preferred embodiment, D-HAF is a single daily application provided by a licensed ophthalmic profession for in-home use by patients. Therefore, nonsurgical ophthalmologists and Optometrists can dispense and oversee the therapy, giving patients greater choices and access to treatment. In addition, unlike the surgical application of HAM, daily applications of D-HAF deliver a sustainable level of beneficial growth factors. Further, D-HAF requires much less manipulation during processing and is sterilized without the harsh terminal irradiation or e-beam required for HAM.

As demonstrated by the applications, the concentration and dosage (number of times per day of amount of formulation for period of time) will vary depending on the condition to be treated, the severity of the condition, and the inclusion of other therapeutic, prophylactic or diagnostic agents. The appropriate amounts are determined on an individual basis, measuring response to treatment over time, as demonstrated in the examples. In most cases, two to three drops of solution will be administered once or twice daily as needed.

The dilution ratio of the D-HAF will be dependent on the severity of the disorder or injury; for example, early to moderate dry eye or chronic redness, surface inflammation and, intraocular inflammation may be best treated with a low concentration, whereas, Sjogren's Syndrome, severe Dry Eye, a corneal neovascular disorder, or corneal opacity may dictate a higher concentration of D-HAF.

In the case of sustained or controlled release formulations, ointments, implants or injections into the eye, the dosages will be modified to deliver a therapeutically equivalent amount.

The present invention will be further understood by reference to the following non-limiting examples. The examples showing preparation of human amniotic formulation are from US20150025366.

Example 1: Preparation of Human Amniotic Formulation

Materials and Methods

Human amniotic fluid is collected from selected caesarean sections, which make aspiration of the amniotic fluid in clean condition possible. Then the amniotic fluid is stored in refrigerated condition at 2° C. to 6° C. before the clarification and filtration process. The amniotic fluid is centrifuged at 5,000 to 10,000 rpm for 30 minutes to 1 hour in 50 mL to 250 mL swing out buckets. The supernatant is collected. When collecting the supernatant it is important to avoid detaching or aspirating insoluble components possibly coming from the pellet or from the fatty overlayer. If the supernatant still contains residual insoluble components, it may be pre-filtered with 5 to 10μ cellulose ester capsule pre-filters without TRITON® surfactant to avoid contamination in the filtration process. The liquid phase is collected and filtered with poly ether sulfone 1.0μ capsule filters and the liquid is collected. The liquid is then filtered with poly ether sulfone 0.2μ capsule filter. The filtrate is transferred to vials and sealed with stoppers aseptically. Four samples from the final filtrate are taken to test whether the sterile filtered human amniotic fluid retains growth factors, such as human growth hormone, transforming growth factor beta 1, vascular endothellal growth factor, epidermal growth factor, transforming growth factor beta 3.

The amniotic fluid from the final filtration is aseptically transferred to syringes or vials, then kept in a deep freezer at about −80° C. to about −20° C. for long term storage. The sterile amniotic fluid is dried in the vial via lyophilisation in a built-in a sterile environment. The lyophilisate derived from the amniotic fluid is reconstituted with sterile water before its injection or topical administration. The lyophilisate can be stored at from +4° C. to about +25° C. (room temperature). All of this operation may be carried out in sterile condition and does not need additional sterilization methods such as a final irradiation.

If needed, the lyophilisate derived from amniotic fluid through lyophilisation may be irradiated by e-beam irradiation or gamma ray irradiation to add another guarantee for the final sterility of the powder. Irradiation of a lyophilisate is much less denaturing for proteins and peptides than irradiating aqueous solutions, because the absence of water considerably reduces the production of reactive superoxide anions and their diffusion during irradiation. Such superoxide anions are the main cause of splitting peptide bonds and chemically modifying amino acids of protein and peptides. After lyophilisation, the amniotic fluid is reconstituted by adding the initial volume of water. After gentle homogenization, the powder is quickly dissolved in about one minute.

Results

The results show retention of growth factors. The concentration of the growth factors in the sterile filtered amniotic fluid is from about 30 pg/mL to about 2500 pg/mL. Except the vascular endothelial growth factor in sample 2, the concentrations of all the factors in the four samples are in the range of 30-150 pg/mL. Although part of growth differentiation factor 11 is lost in centrifugation and filtration, the final sterile filtered amniotic fluid still retains about 17% to 29% of growth differentiation factor from the raw human amniotic fluid.

The reconstituted amniotic liquid is transparent and may be used for wound healing, cosmetic, orthopedic, or ophthalmic applications, particularly for the treatment of dry eyes.

Example 2: Treatment of Dry Eye Patients with Amniotic Fluid Solution

Materials and Methods

Dr. M. Dieter initiated a non-scientific case study utilizing FOY™ REGENER-EYES®, Amniotic Fluid Ocular Solution, prepared as described in Example 1. Dr. Dieter is a licensed Optometrist, specializing in the treatment of Dry Eye Syndrome. Regenerative Processing Plant supplied several samples of Regener-Eyes to Dr. Dieter to distribute to a select group of his patient suffering from the discomfort and pain often accompanied with dry eyes.

The study was designed for ten patients. Three (3) patients entered too late to effectively chart their results. Ultimately, nine (9) patients were officially enrolled in the study.

Study patients were given a 30 day sample of REGENER-EYES® and instructed to add the therapy of 1-2 drops of REGENER-EYES® into both eyes twice daily (a.m. and p.m.), to their current prescribed treatments. The study included the following visual conditions:
Glaucoma
Chronic Dry Eye
Moderate Dry Eye
Mild Dry Eye
Sjogrens Disease
Declining sight
Ankylosing spondylitis (possible)
The following observations were tracked and recorded:
OSDI Scores
Visual Acuity
Redness
Staining degree
Tear Break-up Times
Appearance
Artificial Tears frequency of use
Patient comments The Ocular Surface Disease Index (OSDI) was used to determine the base degree of Dry Eye being experienced by the participants.

Results

The OSDI scores showed consistent improvement with the addition of REGENER-EYES® to the daily treatment plans. For example, one patient's base score was 47.7. After 2 weeks of treatment the score was reduced to 35, after 3 weeks; 27. This was the general trend with all participants in the study. Visual Acuity improvement was nine (9) participants demonstrated improvement in their visual acuity and consistently demonstrated improvement in distance, visual clarity and reading ability. Improvements of one to several lines on the Snellen Eye Chart were also recorded. Visual acuity seemed to be correlated to corneal integrity levels.

REGENER-EYES® AF Ocular Solution appears to have a beneficial impact on improving the corneal epithelial integrity which is important for visual acuity. A common complaint associated with Dry Eye is visual fluctuations. Irregularities in the corneal surface is the most accepted explanation for this phenomena and REGENER-EYES® demonstrated positive assistance for this particular issue.

Redness of the eye is often associated with severe dry eyes. 8 of the 9 participants in this study were classed with severe dry eye and noted improvement in their level of injection.

Staining levels as rated by the Oxford Method, showed improvement in all participants. One participant listed as moderated dry eye, showed no signs of dry eye after the REGENER-EYES® therapy. Over-all, reduction as opposed to elimination in staining would be most accurate in describing the universal results. REGENER-EYES® demonstrated therapeutic benefit for corneal staining with the unexpected decline in the associated use of artificial tear solution for the participants.

Tear Break Up Times (TBUT) are difficult to measure in the limited time of the study. The return of goblet cells to normal levels required extended management of the patient's disease. However, REGENER-EYES® which persists on the ocular surface for 90 seconds is likely to have a major contributory effect on the hypermolarity level.

Participants in this study, presented with signs of discomfort, high blinking frequency, squinting and other subnormal appearances to their eyes. Within 2 weeks of initiating the REGENER-EYES® therapy, 8 of 9 participants had demonstrable improvement in their abnormalities.

A surprising benefit of the REGENER-EYES® Ocular Solution was the expedience in their desire to reduce the use and frequency of an artificial tears solution. One participate classed as Moderate Dry Eye, quit using her artificial tears 3 weeks into the therapy. Others expressed a desire to reduce or eliminate their use of regular artificial tear solutions as well.

Dry Eye Disease continues to be a condition that has no existing cure but must be managed to provide health, well-being and relief to its victims. There has been a widening gap in the therapeutic treatment options for severe dry eye, particularly for the autoimmune aqueous deficient patient. REGENER-EYES® demonstrated benefits which could augment or possibly replace current forms of dry eye therapy for these patients, as well as, milder forms of the disease.

Example 3: Comparative Study on Treatment of Corneal Inflammation

Materials and Methods

The lyophilized powder of Example 1 was dissolved in 1 mL of sterile water to reconstitute 1 mL of the initial sterile filtered amniotic fluid. Two drops were applied on each eye of ten patients suffering from the dry eye syndrome. This treatment was repeated twice per day for ten days. Two other control groups of 10 patients similarly received either their own serum or a serum prepared from cord blood as described by Kyung-Chul Yoon (Umbilical cord and its blood: A perspective on its current and potential use in Ophthalmology, in "Regenerative Medicine Using Pregnancy-Specific Biological Substances" Springer ed. 2011).

Results 8 to 10 patients out of 10 in each group declared that they had experienced a significant benefit. For all patients, this clinical improvement was correlated with a partial or complete decrease of their initial corneal inflammation. Nine patient had "severe" dry eye, one was "moderate." The latter is a 70 year old woman, still working, at a computer all day, who has had dry eye for many years, as well as a long history of allergies, asthma, uses an inhaler as well as an antihistamine, and has had the red eyes associated with this problem. The treatment eliminated the redness and significantly reduced light sensitivity and need for artificial tears. The treatment also restored her ability to read books.

Example 4: Treatment of Glaucoma

A 90 year-old female patient with glaucoma had been on topical medications for glaucoma. Prior to the study, she had declining vision, persistent central corneal staining and suffered from general dry eye for many years due to incomplete blinking patterns and a tendency to sleep with her eyes partially open. She completed a six-week therapy of amniotic fluid drops (twice a day) along with artificial tears. Artificial tears were used eight times a day with a reduced frequency over the period of 6 weeks.

Staining patterns clearly improved after the six-week application but did not resolve completely. Her visual acuity and reading ability improved and as well as her comfort level.

| Patient | OSDI | | OD VA; TBUT (sec); Schirmer | | OS VA; TBUT; Schirmer | |
|---|---|---|---|---|---|---|
| #1 | Before | After | Before | After | Before | After |
| G.G. | 52.5 | 21.87 | 20/40; 4; – | 20/30; 2; 12 | 20/40; 2; – | 20/30 – 2; 2; 12 |

OSDI: the dry eye ocular surface disease index
OD: oculus dexter, the right eye; OS: oculus sinister, the left eye.
VA: visual acuity.
TBUT: the tear break up time, the time it takes for the tear film to start evaporating. The longer it takes for the tear film to break up, the more stable the tear. Schirmer's test determines whether the eye produces enough tears to keep it moist.

Example 5: Treatment of Age Related Eye Degeneration

An 81 year-old female patient presented with a poor physical appearance due to closed eyes, minimal eye contact and generally downward posture. Prior to the study, she constantly complained about eye discomfort and sensitivity to light. She had uncontrolled dry eye for the past 10 years and had tried multiple types of therapy with no obvious improvement. Debris and scurf were observed on her eyelids and eyelashes. She had dementia and was under assisted living condition. She completed a four-week therapy of amniotic fluid drops (twice a day) along with artificial tears. Artificial tears were applied many times a day, depending on the aid's availability with a reduced frequency over the period of four weeks. Additional methods were used along with the eye drops, including hot lid soaks, gentle cleaning and use of artificial tears of preservative-free variety.

After the therapy, both the patient and her care givers noticed significant improvement in the comfort level and life style.

| Patient | OSDI | | OD VA; TBUT (sec); Schirmer | | OS VA; TBUT; Schirmer | |
|---|---|---|---|---|---|---|
| #2 | Before | After | Before | After | Before | After |
| E.G. | 58.3 | 33 | 20/40; 4; 6 (unsure) | 20/30; 4; 3 | 20/40; 4; 6 (unsure) | 20/30; 4; 3 |

Example 6: Treatment of Moderate Dry Eye

A 71 year-old female patient with moderate dry eye resulted from sustained work at a computer for the past 20 years. She had not attained a very comfortable level with the traditional dry eye treatment and had been seeking better therapy. She had a history of allergies. She completed a four-week therapy of amniotic fluid drops (twice a day) along with artificial tears. She used artificial tears more than eight times a day initially with a gradual declining frequency over time.

After the therapy, she observed great improvement in her eye condition. She reached homeostasis and her eyes were comfortable throughout the day. She was almost free of dry eye conditions towards the end of her therapy period although she felt further improvement if the drops were used.

| Patient | OSDI | | OD VA; TBUT (sec); Schirmer | | OS VA; TBUT; Schirmer | |
|---|---|---|---|---|---|---|
| #3 | Before | After | Before | After | Before | After |
| L.J. | 37.5 | 10.41 | 20/20; 5; 10-11 | 20/20; 8; 16 | 20/20; 5; 11 | 20/20; 8; 16 |

Example 7: Treatment of Sjogrens Syndrome

A 77 year-old female patient with Sjogrens syndrome and dry eye condition for 20 years was treated. She had an overall good appearance, mild injection and anterior blepharitis grade-1 mild stye on superior left lid which was resolving. Prior to the study, she had declining vision along with uncomfortable dry eyes. She completed a five-week therapy of amniotic fluid drops along with artificial tears. Amniotic fluid drops were applied two times a day for the first three weeks, followed by three times a day for the rest of the therapy period. Artificial tears were applied inconsistently throughout.

This patient improved in a number of areas including comfort, appearance, light-sensitivity, ability to read, general seeing ability, clinical staining signs, and had a number of positive comments to say about the outcome. An improvement was noted by this patient very early in the therapy, and the cumulative improvement was appreciated by the patient in the above listed ways as the therapy progressed.

| Patient | OSDI | | OD VA; TBUT (sec); Schirmer | | OS VA; TBUT; Schirmer | |
|---|---|---|---|---|---|---|
| #4 | Before | After | Before | After | Before | After |
| E.L. | 70.8 | 31.25 | 20/40; 2; 2 | 20/40 + 2; 4; | 20/50; 2; 2 | 20/30; 3; 1+ |

Example 8: Treatment of Dry Eyes

A 64 year-old female patient with dry eyes as a result of her hysterectomy at the age of 38 was treated. She had been diabetic for the past 25 years and had been using metformin. She also had rheumatoid arthritis. Prior to the study, she was less than comfortable in appearance and semi-squinting constantly. In addition, she also had complaints of scratchy, sore and burning eyes. She completed a four-week therapy of amniotic fluid drops (twice a day) along with artificial tears.

The use of artificial tears declined over time. She had a much improved vision, sunlight sensitivity, comfort levels and appearance after therapy.

| Patient | OSDI | | OD VA; TBUT (sec); Schirmer | | OS VA; TBUT; Schirmer | |
|---|---|---|---|---|---|---|
| | | | | After | | After |
| #5 | Before | After | Before | 3.5 wks | Before | 3.5 wks |
| L.Z. | 77 | 8.3 | 20/40–; 3; 3 | 20/40; 4; 2 | 20/50; 3; 1 | 20/40–; 4; 2 |

Example 9: Treatment of Dry Eyes and Mouth

A 40 year-old female patient diagnosed with Sjogrens syndrome in 2003 was treated. She noted dry mouth and subsequently dry eye problems. She was overall in good health with no joint pain or swelling, although her appearance was uncomfortable with constantly squinting and blinking. She had severe light sensitivity and burning sensation in her eyes. She preferred to keep her eyes closed if possible. She completed a four-week therapy of amniotic fluid drops (twice a day) along with artificial tears. Artificial tears were applied eight times a day for four weeks.

After the therapy, the patient reported improvement in redness and light sensitivity, comfort level and abilities. Clinical examination identified a significant staining present, suggesting analgesic benefits to the eye drop that suppress the clinical evidence of corneal staining.

| Patient | OSDI | | OD VA; TBUT (sec); Schirmer | | OS VA; TBUT; Schirmer | |
|---|---|---|---|---|---|---|
| #6 | Before | After | Before | After | Before | After |
| B.M. | 47.7 | 12.5 | 20/50; 1; 1 | 20/40−; 2; 1-2 | 20/40; 1; 1 | 20/40; 2; 1-2 |

Example 10: Treatment of Dry Eye and Light Sensitivity

A 59 year-old female patient with questionable health conditions was treated. She had a recent weight loss with unexplained reasons, chronic back pain from previous injury as well as rheumatoid arthritis. Prior to the study, she had dry eye for more than 10 years along with a severe light sensitivity. She also had mild redness in her eyes, swollen superior lid appearance and clumping of eyelashes due to anterior blepharitis. She complained of severe discomfort in her eyes and had no relief from traditional artificial tears. The chief source of her problem was the meibomian gland dysfunction of the "obstructive" type that rendered her inadequate protection of tear evaporation. She completed a four-week therapy of amniotic fluid drops (twice a day) combined with artificial tears. Artificial tears was used 10 times a day but was later reduced to three times a day during the therapy period.

An improvement in appearance and comfort levels was observed upon the completion of the therapy.

| Patient | OSDI | | OD VA; TBUT (sec); Schirmer | | OS VA; TBUT; Schirmer | |
|---|---|---|---|---|---|---|
| #7 | Before | After | Before | After | Before | After |
| B.D. | 95.8 | 54 | 20/40; 5; 4 | 20/40; 8; 10 | 20/40; immediately; 5 | 20/30; 8; 10 |

Example 11: Treatment of Sjogrens Syndrome

A 74 year old female patient with Sjogrens syndrome and a severe dry eye condition was treated. She had been forced to compromise some areas in her life such as driving, reading etc.

After a five-week therapy of amniotic fluid drops (twice a day) combined with artificial tears (six to eight times a day), she commented that she was able to drive and that her light sensitivity improved after four and a half weeks after therapy and that she started reading again after years of inability to do so after five weeks after therapy.

| Patient | OSDI | | OD VA; TBUT (sec); Schirmer | | OS VA; TBUT; Schirmer | |
|---|---|---|---|---|---|---|
| #8 | Before | After | Before | After | Before | After |
| J.P. | 58.3 | 20.8 | 20/30 (4 days into therapy); 4; 1 | 20/25; 4-5; 1-2 | 20/20-2 (4 days into therapy); 4; 1 | 20/20; 4-5; 1-2 |

Example 12: Treatment of Glaucoma

An 80 year-old female patient with glaucoma for 10 years, experiencing loss of vision and dry eye, was treated. After a five and a half-week therapy of amniotic fluid drops (twice a day) combined with artificial tears (six times a day), her reading ability, eye staining, dry eye symptoms and standard examination scores have improved.

She had been unable to read prior to therapy, and was back to reading after therapy. She had significant central and inferior corneal staining in punctate and patches prior to therapy, and the patches were all cleared with only less serious punctate fine staining after therapy. She had superficial cornea edema appearing three weeks after therapy, which vanished with a mild hypertonic solution. For alleviating edema, the topical glaucoma medication could be removed and changed to oral acetazolamide in the future.

| Patient | OSDI | | OD VA; TBUT (sec); Schirmer | | OS VA; TBUT; Schirmer | |
|---|---|---|---|---|---|---|
| #9 | Before | After | Before | After | Before | After |
| E.D. | 54 | 22.7 | 20/60; 4; 9 | 20/50+; 6; 10 | 20/60 + 3; 4; 6 | 20/25; 6; 12 |

Overall Summary of the Studies:

Amniotic fluid eye drops provide definite and real improvement for dry eye. Artificial tears have been the mainstay of dry eye therapy and patients would report the drops are of help to their condition, while most clinicians feel they offer no therapeutic benefit. Amniotic fluid eye drops features immediacy benefits, e.g. within four days of use, and cumulative improvement as therapy progresses. Patients quickly begin to make lifestyle changes by venturing out more, are not as hindered, note improvements in performance and sustainability during tasks such as using a computer or the ability to stay up later in the evening. Patients' attitudes improve and expectations rise as they sense greater comfort and greater freedom in life, and people are pleased now and at a point of homeostasis. Cosmetic enhancements are noted with all patients due to less injection of bulbar and palpebral conjunctiva. Improvements are noted among a difficult subset of people knows as severe dry eye patients.

Severe dry eye patients often present with compromised appearances due extreme discomfort. Indications of this are habitual squinting, gaze in downward position vs straight ahead, listening to conversation with eyes closed instead of eyes open with good eye contact, high blinking frequency, etc.

A noticeable change in the appearance was apparent in patients in these studies by the end of two weeks of therapy. Other people would comment to these patients that their eyes were looking better. Most patients expressed improvements and increased comfort with therapy. Most patients expressed satisfaction and interest in continuing on the therapy. The majority of the 9 patients studied showed improvements in light sensitivity. One patient reported after two weeks of therapy being able to return to driving after years of avoiding it due to eye discomfort from dryness, sunlight, etc.

The dry eye ocular surface disease index (OSDI) showed a general trend of improvement in OSDI scores was noted as therapy continued.

Frequency of artificial tear use among patients showed a general trend that patients will use less artificial tears after initiating this therapy. This was a surprise early in therapy, often volunteered without prompting. Despite the patients "feeling" like they do not need their previous artificial tears as much as prior to amniotic eye drop therapy, there is objective evidence the patient may benefit from the use more than they are aware. The advantages some artificial tears are meant to provide seem to still benefit the patient, even when the patients are experiencing a new level of soothing and comfort from the use of amniotic drops. Supplemental therapy with artificial tears for the moderate dry eye patient, who had no objective clinical evidence of dry eye remaining after three weeks of therapy, showed further improvement in comfort when artificial tears were applied. This observation verifies the hypothesis of what amniotic eye drops may not accomplish in dry eye therapy. Amniotic fluid is helpful and beneficial in ways other therapies have not attained, but the forces of evaporation still present challenges to the ocular surface which are aided by this type of therapy control and management.

Improved reading performance was noted in the majority of the patients, while the other patients had early cataracts developed prior to therapy. Improvements in visual acuity (VA) were noted in the majority of the patients with at least one line on the Snellen chart and in others, two or more. Visual acuity improvements seem closely correlated to corneal integrity levels. When central corneal integrity is compromised as evidenced by corneal staining, visual acuity levels are also compromised. As corneal integrity improves with good therapy, visual acuity also improves as indicated. Amniotic fluid eye drops help heal the corneal surface integrity issues, but are not expected to rehydrate these tissues, and traditional methods of dry eye care may still be advantageous to treat this aspect of dry eye disease.

All patients demonstrated improvements in palpebral and bulbar injection levels in essentially all patients within the study.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of treating, alleviating, or preventing a disorder, a disease, or an injury associated with the eye comprising administering to the eye an effective amount of a sterile serially filtered de-cellularized human amniotic fluid (D-HAF) devoid of all amniotic stem cells, insoluble elements of micronized membrane, and chorion particles,
thereby treating, alleviating, or preventing one or more symptoms associated with the disorder, disease, or injury associated with the eye;
wherein the D-HAF is not heat-treated, chemical treated, or gamma-irradiated, and is sterilized only by filtration;
wherein the D-HAF is administered with or without implementation of an implant; and
wherein the D-HAF is administered in a form selected from the group consisting of a solution, a suspension, an ointment, a gel, a spray, and a droplet.

2. The method of claim 1 wherein the D-HAF is administered with implementation of an implant.

3. The method of claim 1 wherein the D-HAF is administered with a pharmaceutically acceptable carrier.

4. The method of claim 1 wherein the D-HAF is administered prior to, in conjunction with, or subsequent to, treatment with one or more therapeutic, prophylactic or diagnostic agents.

5. The method of claim 4 wherein the one or more therapeutic, prophylactic or diagnostic agents are selected from the group consisting of anti-glaucoma agents, antiangiogenesis agents, anti-infective agents, anti-inflammatory agents, analgesic agents, local anesthetic agents, growth factors, immunosuppressant agents, anti-allergic agents, antioxidant agents, and cytokine agents.

6. The method of claim 1 wherein the eye disorder is selected from the group consisting of dry eye disease, ocular burns, tears or injury to the eye or associated structures, corneal neovascular disorders, corneal, opacities, ocular blast injuries, eye infections, drug-induced eye conditions, and prolonged redness and inflammation of the eye.

7. The method of claim 6 wherein the eye disorder is selected from the group consisting of amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post corneal transplant rejection, autoimmune uveitis, infectious uveitis, anterior uveitis, posterior uveitis, pan-uveitis, inflammatory disease of the vitreous or retina, endophthalmitis, macular edema, macular degeneration, age related macular degeneration, proliferative and non-proliferative diabetic retinopathy, hypertensive retinopathy, autoimmune disease of the retina, primary and metastatic intraocular melanoma or other intraocular metastatic tumors, open angle glaucoma, closed angle glaucoma, pigmentary glaucoma and combinations thereof.

8. The method of claim 1 wherein the eye disorder is injury, burn or abrasion of the cornea, cataracts or age related degeneration of the eye or vision associated therewith.

9. The method of claim 1 wherein the eye disorder is dry eye.

10. The method of claim 1, wherein the injury associated with the eye is due to an eye surgery.

11. The method of claim 1, wherein the D-HAF has a 10-6 sterility assurance level.

12. The method of claim 1, wherein the D-HAF is administered in the form of a gel.

13. The method of claim 12, wherein the gel comprises a polysaccharide.

14. The method of claim 13, wherein the polysaccharide is selected from a group consisting of alginate and hyaluronic acid.

* * * * *